(12) United States Patent
Wenchell

(10) Patent No.: US 7,563,250 B2
(45) Date of Patent: Jul. 21, 2009

(54) SELF-SEALING CANNULA

(75) Inventor: Thomas Wenchell, Durham, CT (US)

(73) Assignee: Tyco Healthcare Group, North Haven, CT (US)

( * ) Notice: Subject to any disclaimer, the term of this patent is extended or adjusted under 35 U.S.C. 154(b) by 527 days.

(21) Appl. No.: 10/704,053

(22) Filed: Nov. 7, 2003

(65) Prior Publication Data

US 2004/0162531 A1    Aug. 19, 2004

Related U.S. Application Data

(60) Provisional application No. 60/425,062, filed on Nov. 8, 2002.

(51) Int. Cl.
*A61M 5/178* (2006.01)
(52) U.S. Cl. .................... 604/167.01; 604/264
(58) Field of Classification Search ............ 604/264, 604/23, 93.01, 408, 45, 256, 246, 905, 268
See application file for complete search history.

(56) References Cited

U.S. PATENT DOCUMENTS

| | | | |
|---|---|---|---|
| 3,834,546 A | 9/1974 | Brun et al. | |
| 4,637,396 A * | 1/1987 | Cook | 606/194 |
| 4,655,752 A | 4/1987 | Honkanen et al. | |
| 4,909,798 A | 3/1990 | Feleischhacker et al. | |
| 4,978,341 A | 12/1990 | Niederhauser | |
| 5,071,411 A * | 12/1991 | Hillstead | 604/246 |
| 5,197,955 A | 3/1993 | Stephens et al. | |
| 5,201,714 A | 4/1993 | Gentelia et al. | |
| 5,209,736 A | 5/1993 | Stephens et al. | |
| 5,209,737 A | 5/1993 | Ritchart et al. | |
| 5,226,880 A * | 7/1993 | Martin | 604/99.01 |
| 5,242,412 A | 9/1993 | Blake, III | |
| 5,273,545 A * | 12/1993 | Hunt et al. | 604/256 |
| 5,308,336 A | 5/1994 | Hart et al. | |
| 5,350,364 A | 9/1994 | Stephens et al. | |
| 5,366,478 A * | 11/1994 | Brinkerhoff et al. | 606/213 |
| 5,380,288 A | 1/1995 | Hart et al. | |
| 5,385,553 A | 1/1995 | Hart et al. | |
| 5,407,433 A | 4/1995 | Loomas | |
| 5,411,483 A | 5/1995 | Loomas et al. | |
| 5,476,475 A | 12/1995 | Gadberry | |
| 5,496,280 A | 3/1996 | Vandenbroeck et al. | |
| 5,545,142 A | 8/1996 | Stephens et al. | |
| 5,545,179 A | 8/1996 | Williamson, IV | |
| 5,584,850 A | 12/1996 | Hart et al. | |

(Continued)

FOREIGN PATENT DOCUMENTS

DE    42 31 414 A1    3/1992

*Primary Examiner*—Nicholas D Lucchesi
*Assistant Examiner*—Christopher D Koharski

(57) ABSTRACT

A cannula assembly for performing a surgical includes a cannula defining a longitudinal axis and having a longitudinal passageway extending therethrough, a seal for substantially sealing the longitudinal passageway within the cannula in the absence of an object being received through the passageway and an elongated membrane disposed within the longitudinal passageway of the cannula. The elongated membrane is secured to the cannula at respective ends of the elongated membrane to define an annular space between the elongated membrane and the cannula. The cannula has a throughhole in communication with the annular space whereby, when the cannula is positioned within an insufflated body cavity, insufflation gases pass through the throughhole to expand the annular space to thereby cause the elongated membrane to form a seal about an object inserted therethrough.

6 Claims, 4 Drawing Sheets

U.S. PATENT DOCUMENTS

| | | |
|---|---|---|
| 5,643,911 A | 7/1997 | Yamada et al. |
| 5,709,664 A | 1/1998 | Vandenbroek et al. |
| 5,727,770 A * | 3/1998 | Dennis .................... 251/149.1 |
| 5,752,970 A | 5/1998 | Yoon |
| 5,792,113 A | 8/1998 | Kramer et al. |
| 5,797,888 A | 8/1998 | Yoon |
| 5,871,474 A | 2/1999 | Hermann et al. |
| 5,906,595 A | 5/1999 | Powell et al. |
| 5,993,471 A | 11/1999 | Riza et al. |
| 6,004,303 A | 12/1999 | Peterson |
| 6,123,689 A | 9/2000 | To et al. |
| 6,197,002 B1 | 3/2001 | Peterson |
| 6,238,373 B1 * | 5/2001 | de la Torre et al. .......... 604/256 |
| 6,258,065 B1 | 7/2001 | Dennis et al. |
| 6,276,661 B1 * | 8/2001 | Laird ....................... 251/61.1 |
| 6,358,266 B1 | 3/2002 | Bonutti |
| 6,447,489 B1 * | 9/2002 | Peterson .................... 604/264 |

* cited by examiner

SELF-SEALING CANNULA

CROSS REFERENCE TO RELATED APPLICATIONS

This application claims priority from and the benefits of U.S. provisional application No. 60/425,062 filed on Nov. 8, 2002, the entire contents of which are incorporated herein by reference.

BACKGROUND

1. Field of the Disclosure

The present disclosure relates to a cannula for use in surgical procedures. More particularly, the present disclosure relates to a cannula including a seal assembly adapted to form a seal within a cannula prior to, during and subsequent to insertion of an object through the cannula.

2. Background of Related Art

Minimally invasive surgical procedures have been developed during which surgical instruments are passed through small openings in body tissue to access internal surgical sites. Typically, during these procedures, after an incision has been formed in the body tissue, a cannula defining a lumen is inserted through the incision and positioned in relation to the surgical site. During a laparoscopic procedure, for example, the body cavity is inflated with a nontoxic insufflation gas to create a working area inside a patient for surgical instruments and to allow a trocar to penetrate a body cavity without penetrating an organ within the body cavity. Generally, the cannula includes a sealing member or members to seal the cannula lumen prior to, during, and after insertion of a surgical instrument into the body cavity to prevent insufflation gases within the body cavity from escaping. The sealing member or members often include adjustable sealing elements capable of sealing about multiple instruments of different sizes and shapes.

Although known seal systems for cannulae adequately perform the intended sealing functions, a continuing need exists for a self-sealing system which substantially seals a cannula during all phases of the procedure and which allows for easy insertion and removal of multiple size instruments into and from the cannula.

SUMMARY

A cannula assembly for performing a surgical procedure is disclosed. The cannula assembly includes a cannula defining a longitudinal axis and having a longitudinal passageway extending therethrough, a seal for substantially sealing the longitudinal passageway within the cannula in the absence of an object being received through the passageway and an elongated membrane disposed within the longitudinal passageway of the cannula. The elongated membrane is secured to the cannula at respective ends of the elongated membrane to define an annular space between the elongated membrane and the cannula. The cannula has a throughhole in communication with the annular space whereby, when the cannula is positioned within an insufflated body cavity, insufflation gases pass through the throughhole to expand the space of the annular space to thereby cause the elongated membrane to form a seal about an object inserted therethrough.

Preferably, the elongated membrane includes a material selected from the group consisting of KEVLAR and nylon. In one preferred embodiment, the elongated membrane includes a knitted construction that expands upon the introduction of an instrument inserted therethrough. Alternatively, the elongated membrane may include an elastomeric material. The elongated membrane may be adapted to substantially close the passageway in response to introduction of gases within the annular space and in the absence of an object inserted therethrough.

The elongated membrane may include at least one ridge on an inner surface portion thereof. The at least one ridge is arranged on the elongated membrane so as to occupy a void between the inner surface portion of the elongated membrane and the object to facilitate sealing relation with the object. Preferably, the elongated membrane includes a plurality of ridges radially spaced about the inner surface portion of the elongated membrane.

The throughhole within the cannula is preferably disposed at a distal end of the cannula in an outer wall portion thereof. The cannula may also include a second passage adjacent a proximal end of the cannula and in communication with the annular space to provide fluid to the annular space. The second passage for providing fluid is adapted for fluid connection to an external source of insufflation gases. In one preferred embodiment, the cannula includes a housing and a cannula body extending from the housing, wherein the second passage for providing fluid includes a channel within the housing and in communication with the annular space to permit passage of insufflation gases therethrough.

A method of use of the assembly is also disclosed.

BRIEF DESCRIPTION OF THE DRAWINGS

Preferred embodiments of the present disclosure will be better appreciated by reference to the drawings wherein.

DETAILED DESCRIPTION OF PREFERRED EMBODIMENTS

The principles of the present disclosure are applicable to a variety of surgical access devices adapted for permitting percutaneous access to a target site. These access devices include, but are not limited to, trocars and/or cannulas, catheters, hand access devices, scopes, etc. The present disclosure is contemplated for use in various surgical procedures including, e.g., laparoscopic, arthroscopic, thoracic, etc.

The following discussion will initially focus on the structure and components of the novel access device. A method of use of the apparatus also will be discussed.

In the following description, as is traditional, the term "proximal" will refer to the portion of the instrument closest to the operator while the term "distal" refers to the portion of the instrument most remote from the operator.

Figure 1:
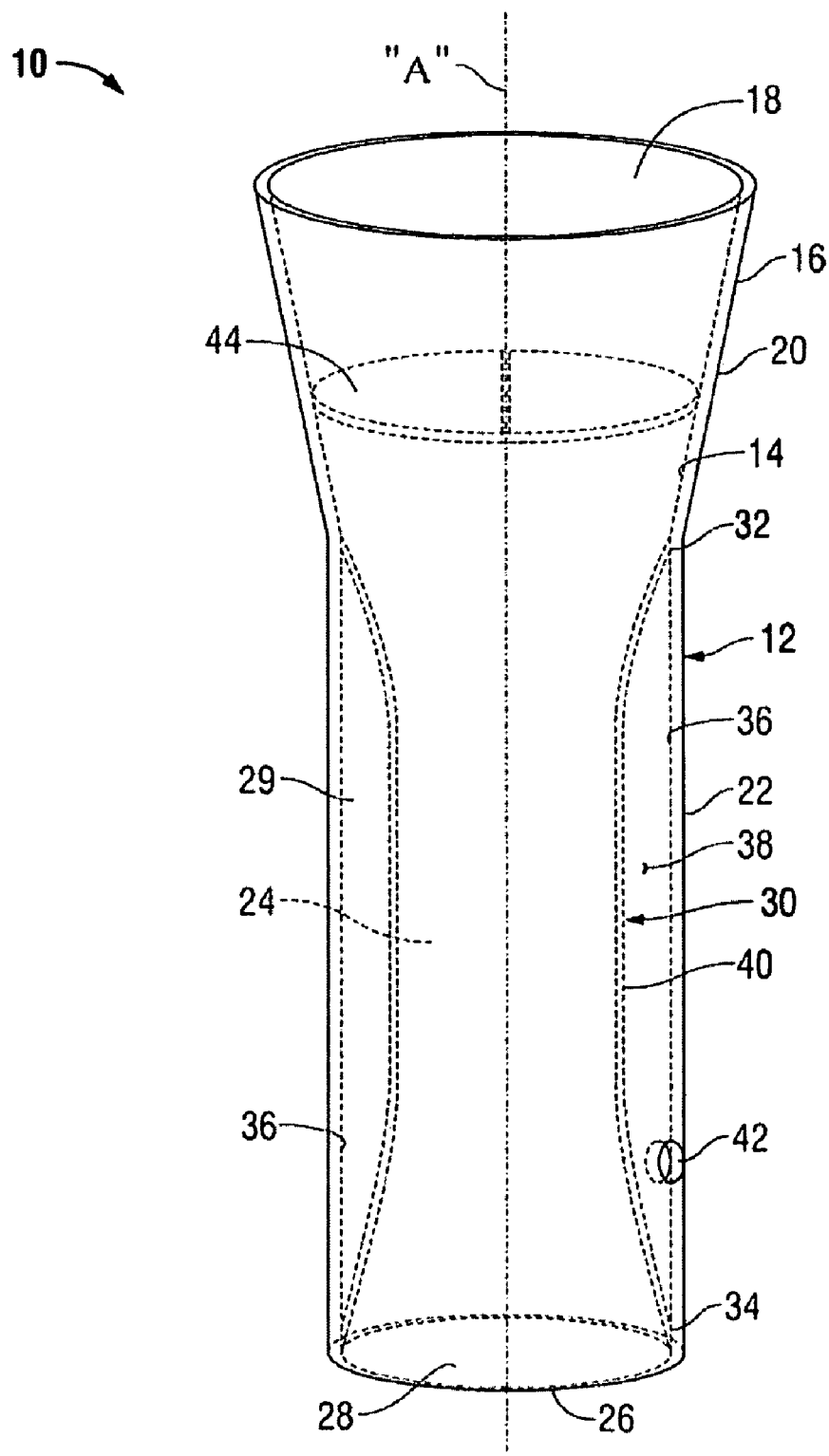
FIG. 1 is a perspective view of a cannula assembly incorporating an elongated seal in accordance with an embodiment of the present disclosure.

The presently disclosed self-sealing cannula assembly or access device, shown generally as 10 in FIG. 1, includes a cannula body 12 defining lumen 14 and longitudinal axis "a". Body 12 includes upper end 16 defining inlet opening 18, a converging or frusto-conical section 20 extending from the upper end 16 and a central body portion 22. Body portion 22 is preferably cylindrical defining an internal lumen 24 (shown in phantom) and having lower end 26. Lower end 26 defines an outlet opening 28. Inlet opening 18, lumen 24 and outlet opening 28 provide a longitudinal passageway 29 for gaining access to a patient's body during surgery.

Body 12 is illustrated as being of monolithic construction; however, it is envisioned that body 12 can be formed of multiple components. Body 12 may be completely cylindrical in configuration although other shapes and dimensions are also envisioned. The preferred materials of fabrication of body 12 include medical grade materials such as stainless steel or any suitable rigid polymeric material. Body 12 may be opaque or transparent.

Referring still to FIG. 1, body 12 includes sheath or membrane 30 mounted therein. Membrane 30 is elongated as shown and defines first and second ends 32, 34. Each end 32, 34 is secured to inner surface 36 of the cannula wall of cannula body 12, preferably, in sealed relation therewith so as to define an annular space 38 between the inner surface 36 of the cannula wall and elongated membrane 30, and define a central interior space 40 along axis "a". Cannula body 12 further includes throughhole 42 which extends completely through the cannula wall in communication with annular space 38 and adjacent both the second end 34 of elongated membrane 30 and lower end 26 of cannula body 12. Although elongated membrane is shown in FIG. 1 with first end 32 at an upper end of central body portion 22 and second end 34 at lower end 26, the membrane 30 need not extend the entire height of the central body portion 22.

Cannula body 12 also desirably includes second seal 44 mounted adjacent upper end 16 of the body 12. Second seal 44 comprises an elastomeric member and has an expandable slit formed therein. Second seal 44 is intended to seal the passageway 29 within cannula body 12 in the absence of an object received in the passageway 29 to thereby maintain the pneumoperitoneum established within the abdominal cavity, i.e., to function as a zero-closure valve or seal. Alternately, other seals types may be utilized including septum seals, gel seals, flapper valves, duck-bill seals etc.

Figure 2:
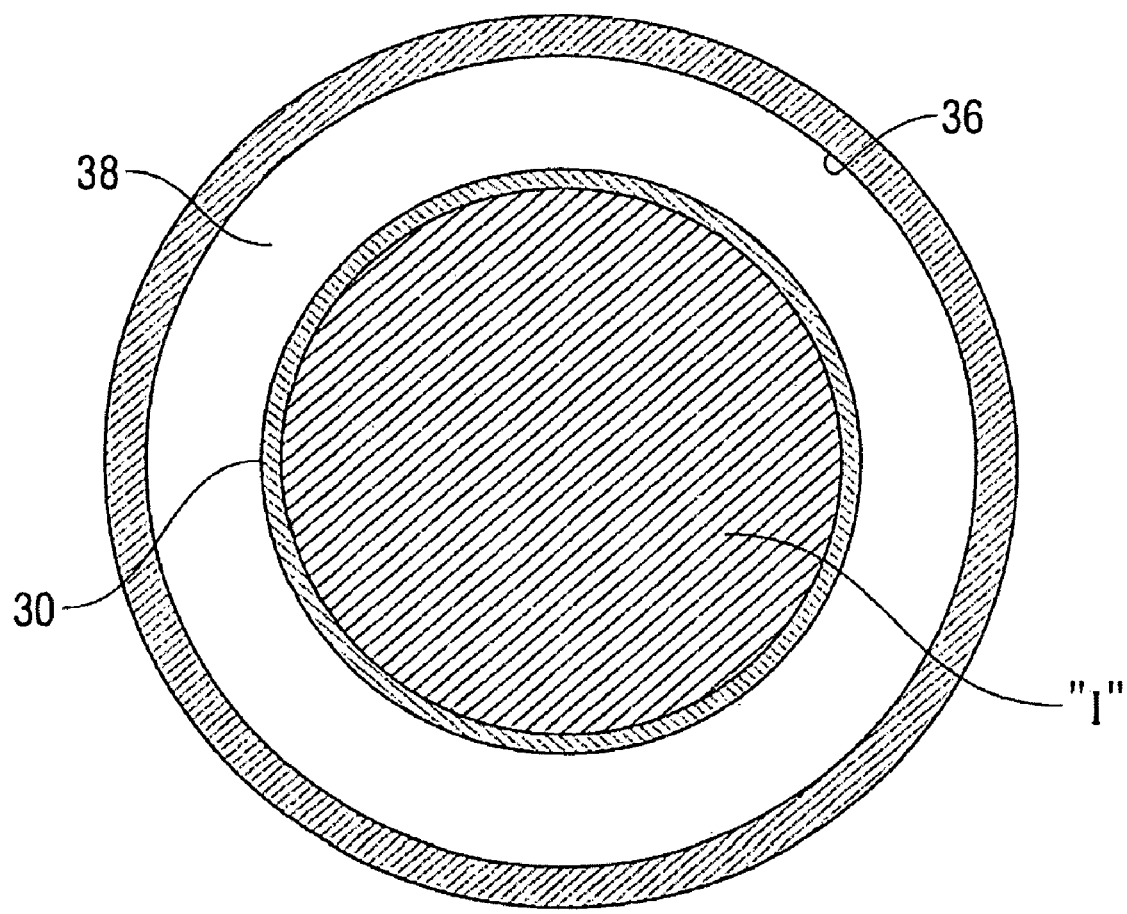
FIG. 2 is a cross-sectional view of the cannula of FIG. 1 illustrating an instrument within the elongated seal.

In use, when self-sealing cannula 10 is positioned through a body incision into an insufflated cavity, pressurized gas from within the cavity flows into annular space 38 via throughhole 42 and expands the annular space 38. Thereafter, an object is inserted through central space 40 formed by elongated membrane 30. Upon insertion, elongated membrane 30 is compressed about the object such as instrument "i", to form a seal about the object as depicted in the cross-sectional view of FIG. 2.

Cannula 10, according to the present disclosure, is self-sealing when it is disposed in an insufflated body cavity. When membrane 30 compresses about an object, a pressure barrier is created at the juncture of membrane 30 and the surgical instrument. This pressure barrier prevents the insufflation gas pressure from escaping the pressurized body cavity. In further embodiments, a separate source of pressure for inflating the membrane 30 and expanding the annular space 38 is used. Such source may comprise a gas or liquid pump.

In the preferred embodiment, elongated membrane 30 is formed from a material that will compress substantially uniformly around the body of a surgical instrument and form the pressure barrier with minimal gaps about the instrument. In certain preferred embodiments, elongated membrane 30 comprises an elastomeric material which is also adapted to expand upon passage of the instrument through the passageway 29 past the membrane. It is preferred that a synthetic material be used, such as nylon, Kevlar® (Trademark of E.I. Dupont De Nemours and Company), or any other material that will compress uniformly when a surgical instrument is inserted in the cannula body 10. The selected material may also be of knitted construction to minimize or prevent wrinkling of membrane 30 when a surgical instrument is inserted into cannula 10. The knitted construction should be substantially impermeable to allow the membrane 30 to be inflated.

Elongated membrane 30 may be formed from natural materials, synthetic materials or a combination of natural and synthetic materials.

The selected material will desirably have a low coefficient of friction so that insertion and removal of the surgical instrument does not require excessive amounts of force. A lubricious coating may be used. Further still, the selected material is preferably thin yet durable enough to prevent the surgical instrument from inadvertently puncturing membrane 30 during insertion, removal or operation of said instrument.

Alternately, the membrane 30 may be formed as a layered structure. Each layer of the membrane 30 may be formed from a different material than another layer, while each layer may also be formed to have a different thickness from another layer. It is considered within the scope of this disclosure that multiple layers may employ the same material in their construction, multiple intermediate layers may be disposed between the inner and outer layers, and other combinations of materials, layers, and thicknesses may be employed.

The membrane 30 may also utilize sections or panels of differing materials arranged along the longitudinal axis of the cannula. One or more panels of material are disposed from the distal end to the proximal end of the cannula. Each panel may be formed from a different material depending on its longitudinal placement. An example of this membrane 30 has an upper panel disposed near the proximal end of the cannula and an attached lower panel disposed near the distal end of the cannula. Furthermore, one or more intermediate panels may be disposed between the upper and lower panels. Each of the panels may be formed from a different material than its adjacent panel and may have a different thickness than its adjacent panel. It is also within the scope of this disclosure to combine the longitudinally oriented panels with the transversely oriented layers discussed previously.

Figure 3:
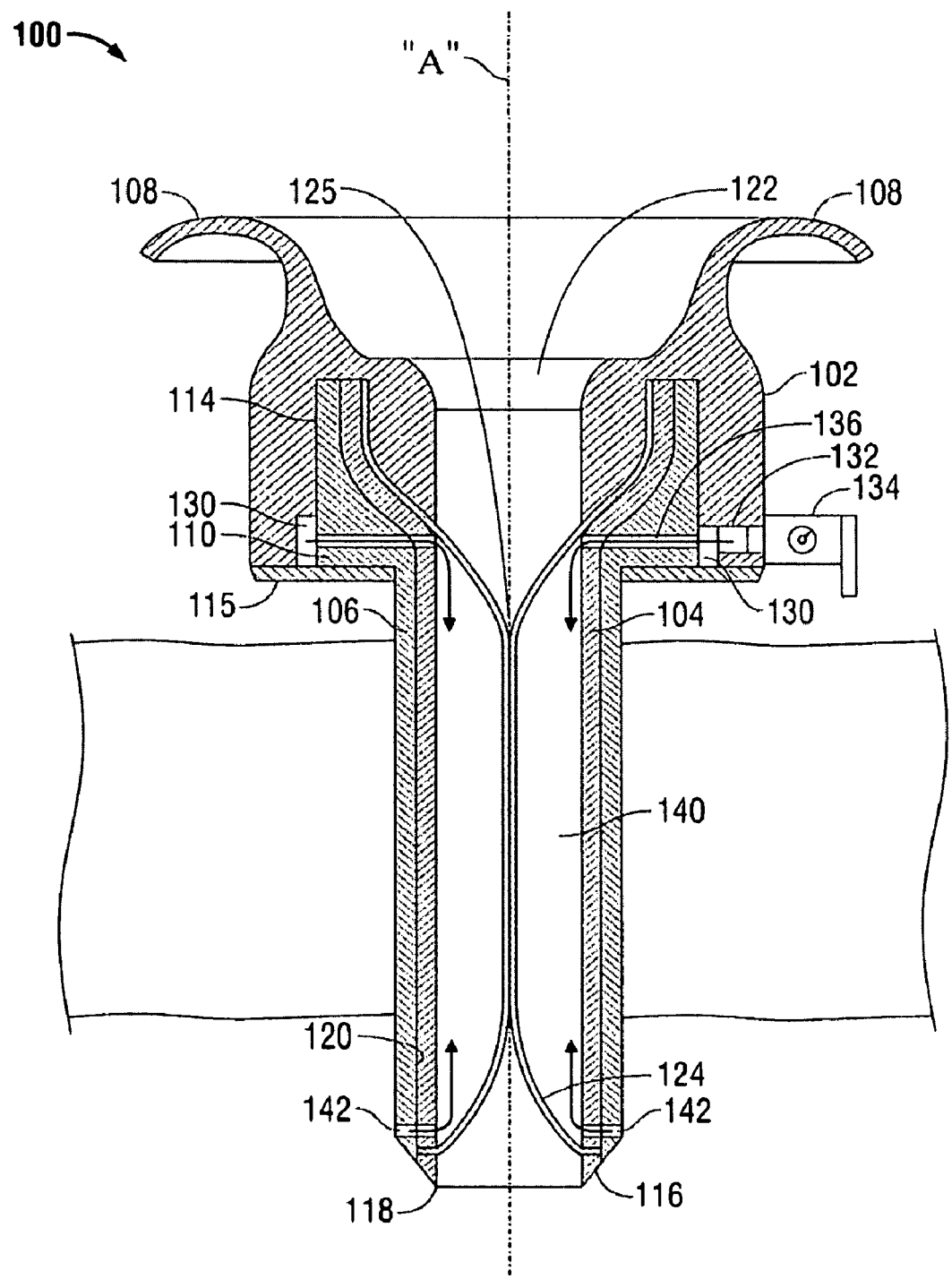
FIG. 3 is a side cross-sectional view of an alternate embodiment of the seal of FIG. 1.

Referring now to FIG. 3, another preferred embodiment of the seal of the present disclosure is shown. Self-sealing cannula assembly 100 includes an upper housing portion 102, and a cannula body having an inner cannula portion 104 and an outer cannula portion 106. Upper housing portion 102 includes a pair of finger grips 108 for grasping by a surgeon. Outer cannula portion 106 includes a proximal portion 110 that defines a shoulder 112 and is configured to be received within an annular recess 114 formed in upper housing portion 102. The distal end 116 of outer cannula portion 106 is tapered and forms an annular edge 118 to facilitate insertion of cannula 100 into a body opening, such as one formed using a trocar. An inner wall of outer cannula portion 106 includes an elongated recess 120 dimensioned to receive inner cannula portion 104. The proximal end of inner cannula portion 104 is also configured and dimensioned to be received within annular recess 114 of housing portion 102.

Inner cannula portion 104 and housing portion 102 define passageway 122. A membrane 124 is supported within passageway 122. The proximal end of membrane 124 is sealingly press fit between housing portion 102 and inner cannula portion 104 within annular recess 114. The distal end of member 124 is sealingly press fit between the distal end of inner cannula portion 104 and the distal end of elongated recess 120. The membrane 122 forms an annular space 140 between inner cannula portion 104 and the membrane 122 and a central space 125 along the longitudinal axis "a" of the cannula assembly 100. In certain embodiments, a zero-seal as discussed above in connection with FIG. 1 may be mounted in passageway 122.

An annular passage 130 is provided within housing portion 102. A first passage 132 extends through housing portion 102 and communicates with annular passage 130. A stopcock valve 134 regulates flow of gas into first passage 132 and, thus, annular passage 130. A second passage 136 is formed through the proximal end of inner and outer cannula portions 104 and 106 and includes a first end communicating with passage 130 and a second end communicating with annular space 140 defined between inner cannula portion 104 and an inner surface of member 124. The distal end of inner and outer cannula portions 102, 104 also include at least one, but preferably two or more, throughholes or passages 142, which extend from outside cannula 100 to annular space 140. The stopcock 134 may be used to introduce insufflation gas into the patient's body, through the throughholes 142 or insufflation may be introduced at another site and permitted to enter the annular space 140 through throughholes 142, to assist in inflating membrane 24.

In use, cannula assembly 100 can operate as a self-sealing cannula in that insufflation pressure from within a body cavity can be used to pressurize annular space 140 via throughholes 142 to form a seal about an object such as a surgical instrument. Alternately, or additionally, pressure to inflate membrane 122 can be supplied to annular space 140 via stopcock valve 134, first passage 132, annular passage 130 and second passage 136.

Figure 4:
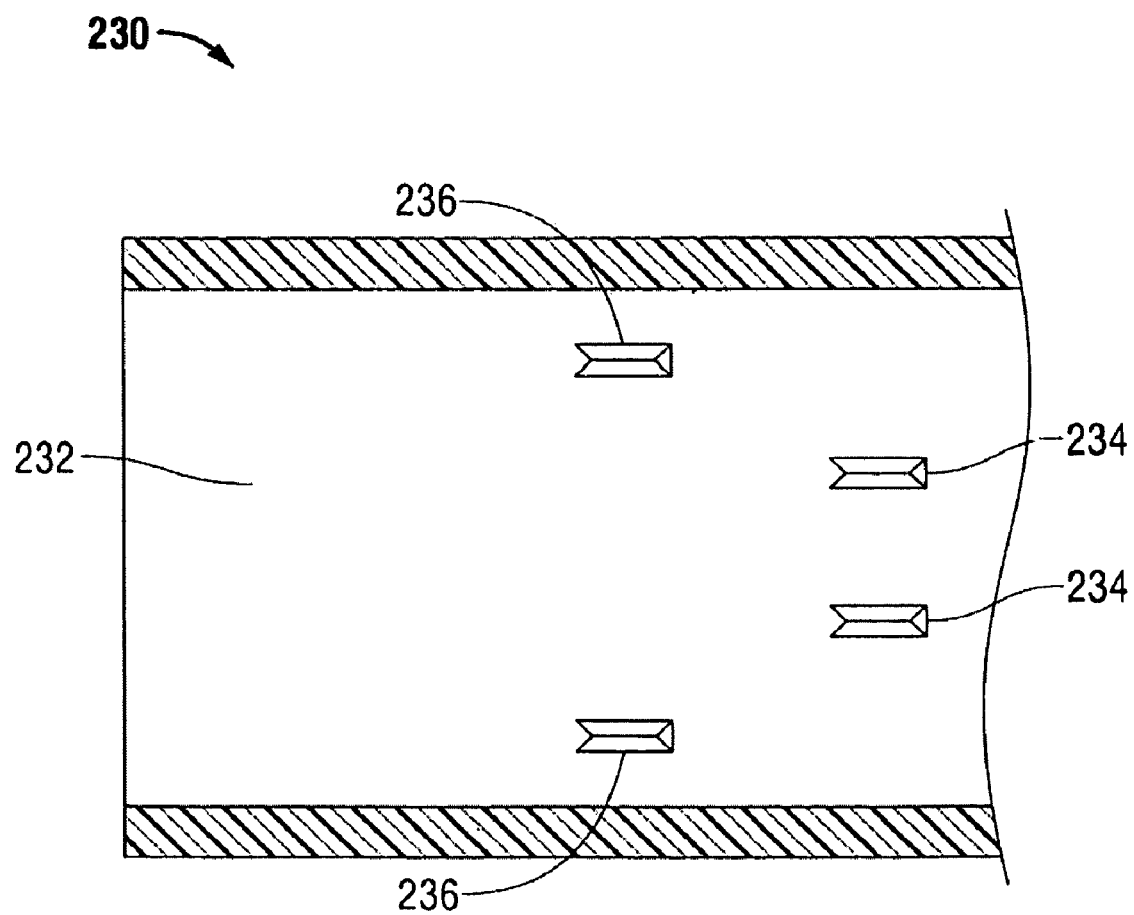
FIG. 4 is a side cross-sectional view of an alternate embodiment of the seal of FIG. 3.

Referring now to FIG. 4, a membrane 230 for a cannula assembly in accordance with further embodiments is shown. In this embodiment, membrane 230 includes an inner wall 232. Inner wall 232 includes a plurality of ridges 234, 236. When cannula 10 is inserted into an insufflated body cavity and an object such as a surgical instrument is inserted into cannula 10, membrane 230 compresses to form a gas-tight seal about the body of the surgical instrument. In the event that the compression of membrane 230 is not uniform about the body of the surgical instrument, ridges 234, 236 will substantially fill any gaps that occur between inner wall 232 and the body of the surgical instrument. The juncture of ridges 234, 236 and the outer surface of the body of the surgical instrument form the pressure barrier for inhibiting leakage of insufflation gases. The ridged structure shown in FIG. 3 is easily adapted to all the embodiments of the subject disclosure. For example, sealing membrane 30 and/or membrane 122 discussed previously could be manufactured with ridges to improve the sealing characteristics. Further still, although ridges 234, 236 are preferably longitudinally oriented along the sealing membrane's inner wall 232, it is within the scope of this disclosure to dispose ridges 234, 236 laterally or at some other orientation along inner wall 232 of sealing membrane 230.

The embodiments shown in FIGS. 1-4 may include or omit the throughholes at the distal end of the assembly. Fluids such as insufflation gas or liquids may be introduced through a passage at the proximal end of the assembly to inflate the membrane.

It will be understood that various modifications may be made to the embodiments disclosed herein. For example, although body 12 is illustrated as having a single throughhole 42, multiple throughholes 42 may be provided as exhibited in the embodiment of FIG. 3. Moreover, throughholes 42 may be positioned at any location along central body portion 22 positioned within the insufflated body cavity. The cannula may also have a variety of different shapes other than cylindrical, e.g., square, oval, rectangular, etc. Inflatable membrane can be fastened to the cannula using any known technique including those not disclosed herein. The cannula assembly may include or omit zero-seal. Therefore, the above description should not be construed as limiting, but merely as exemplifications of preferred embodiments. Those skilled in the art will envision other modifications within the scope and spirit of the disclosure.

I claim:

1. A cannula assembly for performing a surgical procedure within an insufflated abdominal cavity, which comprises:
    a cannula including a cannula housing and a cannula member extending from the cannula housing, the cannula member defining a longitudinal axis and proximal and distal ends, the cannula having a longitudinal passageway extending therethrough;
    an expandable elongated object seal membrane disposed within the longitudinal passageway and at least partially within the cannula member, the elongated seal membrane adapted for expansion from an initial condition to an expanded condition upon introduction of fluids within the elongated seal membrane to establish a sealing relation about an object inserted through the elongated seal membrane, the elongated seal membrane being symmetrically arranged about the longitudinal axis in the initial condition and mounted within the longitudinal passageway to provide a predefined substantially annular space at least between an intermediate portion of the elongated seal membrane and the cannula member when in the initial condition, the annular space adapted to receive fluids to expand the second elongated seal membrane to achieve the expanded condition to establish the sealing relation about the object;
    a fluid passage in fluid communication with the annular space for introducing insufflation fluid into the annular space to expand the annular space to thereby cause the elongated seal membrane to achieve the expanded condition to establish the sealing relation about the object, the fluid passage being a throughhole adjacent the distal end of the cannula and in communication with the annular space whereby, when the cannula is positioned within an insufflated body cavity, insufflation gases pass through the throughhole to expand the annular space to thereby cause the second elongated seal membrane to establish the sealing relation about the object; and
    a closure seal within the cannula housing and proximal of the elongated seal membrane, the closure being adapted to seal the longitudinal passageway in the absence of the object to substantially prevent release of insufflation gases.

2. The cannula assembly according to claim 1 wherein the fluid passage is in fluid communication with an external source of insufflation fluid and in fluid communication with the annular space for introducing insufflation fluid into the annular space to expand the annular space to assist in establishing the sealing relation about the object.

3. The cannula assembly according to claim 1 wherein the elongated seal membrane is further adapted to substantially close the longitudinal passageway in response to introduction of fluids within the annular space and in the absence of an object inserted therethrough.

4. The cannula assembly according to 1 wherein the elongated membrane includes at least one ridge on an inner surface portion thereof.

5. The cannula assembly according to claim 4 wherein the at least one ridge is arranged on the elongated membrane so as to occupy a void between the inner surface portion of the elongated membrane and the object to facilitate sealing relation with the object.

6. The cannula assembly according to claim 5 wherein the elongated membrane comprises a plurality of ridges radially spaced about the inner surface portion of the elongated membrane.

* * * * *